United States Patent [19]
Gisin et al.

[11] Patent Number: 5,280,334
[45] Date of Patent: Jan. 18, 1994

[54] APPARATUS FOR MEASURING CROSS-SECTIONAL DISTRIBUTION OF REFRACTIVE INDEX OF OPTICAL WAVEGUIDE BY RNF METHOD

[75] Inventors: Nicolas Gisin, Geneva; Patrick Stamp, Carouge, both of Switzerland; Nobuo Hori, Tokyo, Japan

[73] Assignee: Kabushiki Kaisha TOPCON, Tokyo, Japan

[21] Appl. No.: 864,628

[22] Filed: Apr. 7, 1992

[30] Foreign Application Priority Data

Apr. 19, 1991 [JP] Japan ................... 3-115481

[51] Int. Cl.$^5$ ................ G01N 21/41; G01N 21/43
[52] U.S. Cl. .................... 356/73.1; 356/128; 356/135
[58] Field of Search .......... 356/73.1, 128, 135

[56] References Cited

U.S. PATENT DOCUMENTS 5,125,740  6/1992  Sato et al. ............... 356/135 X

*Primary Examiner*—Vincent P. McGraw
*Attorney, Agent, or Firm*—Nields & Lemack

[57] ABSTRACT

According to the present invention, there are provided a projection system for emitting luminous flux for measurement, a light receiving unit or a prism member furnished with a light receiving unit, and an optical waveguide substrate comprising a substrate portion and an optical waveguide portion formed on the substrate portion, the light receiving unit or the prism is brought into close contact with the optical waveguide substrate, luminous flux for measurement from the projection system is passed from one end of the optical wavegide portion and a part of the luminous flux for measurement is leaked toward the light receiving unit, whereby cross-sectional distribution of refractive index of the optical waveguide is measured by change of light quantity of the leaking light sensed at the light receiving unit in case an incident point of the luminous flux for measurement is moved.

11 Claims, 6 Drawing Sheets

APPARATUS FOR MEASURING CROSS-SECTIONAL DISTRIBUTION OF REFRACTIVE INDEX OF OPTICAL WAVEGUIDE BY RNF METHOD

BACKGROUND OF THE INVENTION

The present invention relates to an apparatus for measuring cross-sectional distribution of refractive index of an optical waveguide, which is used for optical communication.

As a method for measuring cross-sectional distribution of refractive index of an optical waveguide, there is the refracted near field method (RNF method). This RNF method is non destructive and provides high measurement accuracy and high resolution and is considered as the most excellent method for measuring cross-sectional distribution of refractive index of an optical waveguide.

According to this RNF method, an optical waveguide substrate 1 comprises an optical waveguide portion 3 on one side of the substrate portion 2, and this is immersed in a liquid 9 having refractive index of $n_L$, which is closer to the refractive index $n(r)$ of the optical waveguide portion 3 as shown in FIG. 15. Under this condition, laser beam converged by an objective lens 8 on an end surface of said optical waveguide portion 3 is irradiated at an incident angle $\theta$, and the light leaking through the optical waveguide portion 3 is detected, and the refractive index of the optical waveguide portion 3 is measured.

When the refractive index of the optical waveguide portion 3 at the point where laser beam enters is supposed to be $n(r)$, and that the refractive index of the air or the liquid, of incident side on optical waveguide portion 3 is $n_0$, the exit angle $\beta$ relative to the incident angle $\theta$ is given simply by the following equation (1) in accordance with Snell's law:

$$n^2(r) = n_0^2 \sin^2 \theta + n_L^2 \cos^2 \beta \tag{1}$$

Therefore, when the incident point of laser beam is scanned toward the direction of the thickness of the optical waveguide portion 3, or the direction of crossing at right angles with the above direction, the exit angle $\beta$ changes according to the refractive index $n(r)$ at each point. Specifically, the exit angle $\beta$ is decreased at the portion having higher refractive index, and it is increased at the portion having lower refractive index.

Accordingly, by judging the condition of the leaking light, the refractive index $n(r)$ of the optical waveguide portion 3 can be obtained.

The apparatus for measuring cross-sectional distribution of refractive index of optical waveguide according to RNF method is based on the above principle.

Continuing the explanation in connection with FIG. 15, a detector 5 for receiving the light 4 leaking through said optical waveguide portion 3 is provided on lateral side of the optical waveguide portion 3. Also, a shielding plate 6 of semi-circular disk is provided for shielding a part of the leaking light 4 closer to the center. Said detector 5 receives the leaking light 4 in semi-doughnut shape, lacking a part of said detector 5 closer to the center. The light receiving quantity is given by the following equation (2), where the angle of the leaking light to the light receiving point on the outermost side is $\theta_{max}$ and the angle corresponding to the inner light receiving point shielded by said shielding plate 6 is $\theta_{min}$.

$$P = \int_{\cos\theta_{max}}^{\cos\theta_{min}} I(\theta) \cdot d(\cos\theta) \tag{2}$$

In the above equation, $I(\theta)$ represents intensity distribution based on the angle dependency of the incident light. By sufficiently increasing the light receiving surface of the detector 5, the leaking light 4 is prevented from going out of the light receiving surface. Therefore, $\theta_{max}$ in the above equation (2) is determined by the numerical aperture (NA) and is given by the following equation (3):

$$n_0 \sin \theta_{max} = NA \tag{3}$$

The above exit angle $\beta_{max}$ is changed according to the refracting powder of the optical waveguide portion 3, that is, the light receiving point on the outermost side of the leaking light is moved, whereas it is primarily determined by the point where the detection light enters the optical waveguide portion 3 and also by the position of the edge of said shielding plate 6 and is not influenced by the refractive index of the optical waveguide portion 3.

Further, the incident angle $\theta_{min}$ corresponding to the above exit angle $\beta_{min}$ is obtained by the equation (4), which is a variant of the above equation (1).

$$n_0^2 \sin^2 \theta_{min} = n^2(r) - n_L^2 \cos^2 \beta_{min} \tag{4}$$

The incident angle $\theta_{min}$ is an important factor to determine the refractive index of optical waveguide portion 3. Specifically, the light quantity obtained by the above equation (2) is changed according to the refractive index.

When it is supposed that the light receiving quantity at an arbitrary point in the direction of the thickness of the above optical waveguide portion 3, or the direction of crossing at right angles with the above direction is $P(n(r))$, this light receiving quantity $P(n(r))$ is given by the following equation (5):

$$P(n(r)) = \int_{\cos\theta_{max}}^{\cos\theta_{min}(n(r))} I(\theta) \cdot d(\cos\theta) \tag{5}$$

Next, if the angle dependency $I(\theta)$ of the incident light intensity has Lambert distribution $[I(\theta) = I_0 \cos \theta]$, the equation (6) is obtained from the equation (5), and $\Delta n(r)$ can be obtained when the laser spot position is scanned in the direction of the thickness of the optical waveguide portion, or the direction of crossing at right angles with the above direction and the change of light quantity $\Delta P$ is measured.

$$\Delta P = a \cdot \Delta n(r) \tag{6}$$

Here, the proportional constant $a$ is determined by the refractive index $n_L$, which is already known.

Normally, laser beam is used as the light source. In this case, incident light intensity distribution $I(\theta)$ is Gauss distribution rather than Lambert distribution, and the light quantity change and the change of refractive index are not so simple as in the equation (6). Through the correction by calculation, $\Delta n(r)$ can be obtained.

In a conventional type apparatus for measuring cross-sectional distribution of refractive index of an optical waveguide, the optical waveguide substrate is immersed in a liquid which has the refractive index closer to, or more preferably, higher than that of the optical waveguide portion in order to prevent total reflection of light within the optical waveguide portion and to irradiate the light entering the optical waveguide portion to outside the optical waveguide portion. For this reason, the conventional type apparatus requires the liquid for immersion.

In case the material of optical waveguide portion is glass, the refractive index is about 1.5, and it is relatively easy to select the liquid for immersion. However, in case the optical waveguide portion is formed by thermal diffusion of Ti on single crystal substrate of LiNbO$_3$ or LiTaO$_3$, the refractive power of the substrate is 2.0 or more in many cases.

For such optical waveguide substrate, the liquid for immersion having similar refractive index is needed, whereas the liquid having the refractive index of 2.0 or more is harmful to human body. Also, even when the refractive index is low, there may be no liquid for immersion suitable for the substrate, depending upon the material of the substrate. For this reason, it is diffifult and dangerous to measure, or it is impossible to measure in some cases.

The object of the present invention is to make it possible to measure the distribution of refractive index of optical waveguide even when the liquid for immersion is not provided.

DETAILED DESCRIPTION OF THE PREFERRED EMBODIMENT

In the following, the embodiments of the present invention are described in connection with the drawings.

Figure 1:
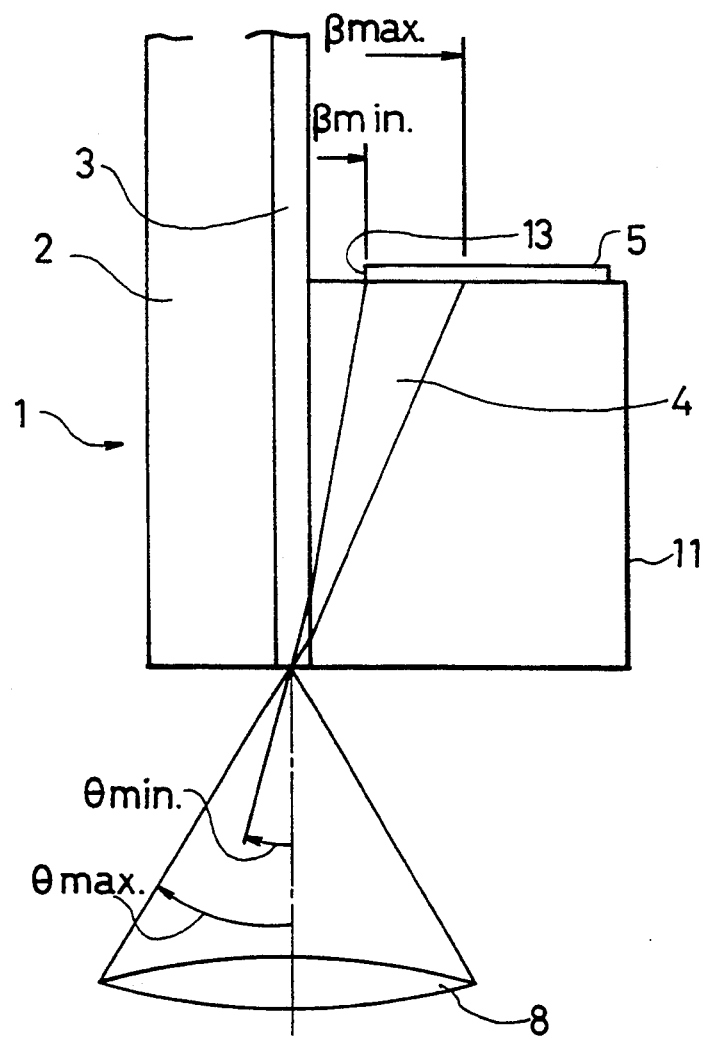
FIG. 1 shows a basic configuration of an embodiment of the present invention.
Figure 15:
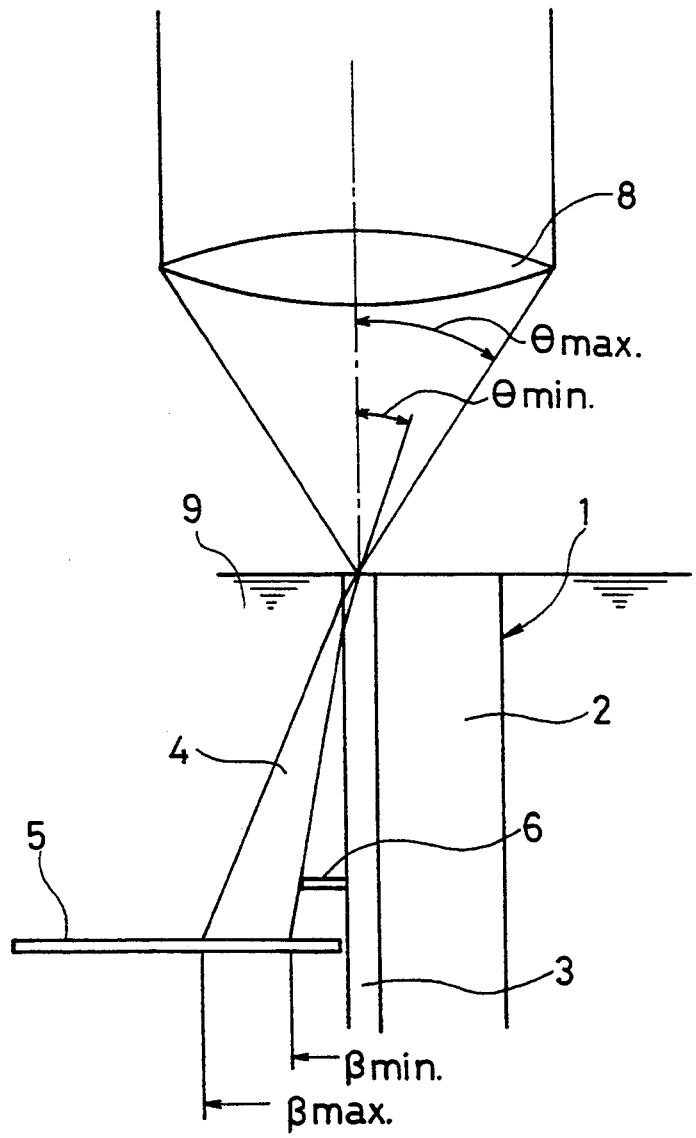
FIG. 15 shows a conventional type example.

In FIG. 1, the same component as in FIG. 15 is referred by the same reference number.

Figure 2:
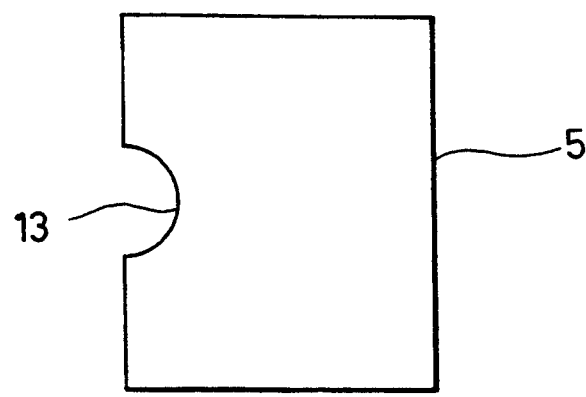
FIG. 2 is a drawing for explaining the shape of a detector in this embodiment.

A cube prism 11 having approximately the same refractive index as that of the optical waveguide portion 3 is mechanically fixed on the optical waveguide portion 3, and a detector 5 is attached on the surface of said cube prism 11 distant from the objective lens. Said detector 5 has a semi-circular notched portion 12 having optical axis on projection side on the end closer to the center as shown in FIG. 2 so that the edge 13 of said notched portion 12 has minimum exit angle $\beta_{min}$ of the leaking light 4.

The refractive index of said cube prism 11 corresponds to $n_L$ of the equation (1), and the basic equation of RNF method is applicable.

Now, description is given on the condition where said optical waveguide portion 3 and cube prism 11 are brought into close contact with each other.

Figure 3:
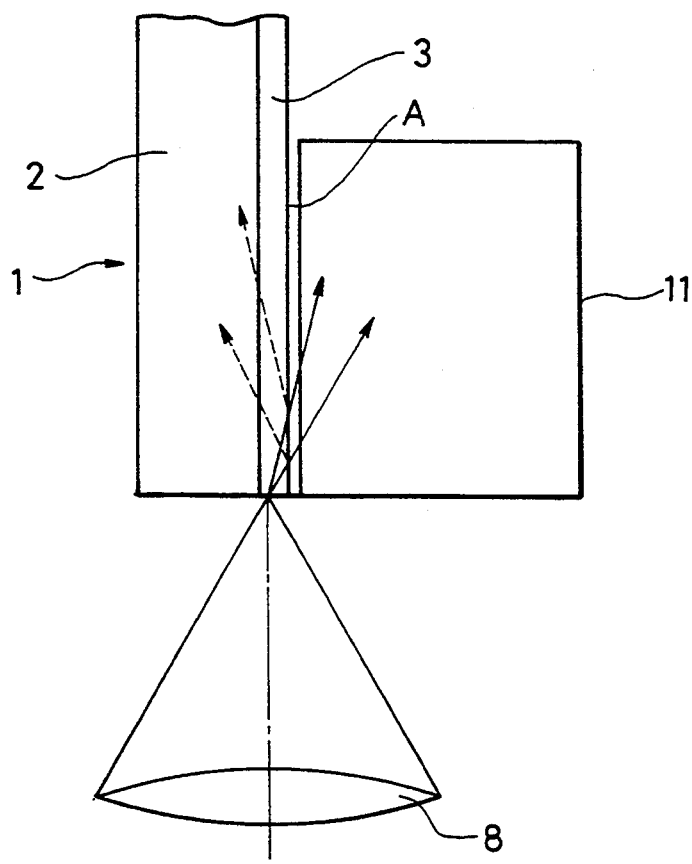
FIG. 3 is a drawing for explaining the transmission of light between the optical waveguide substrate and prism.

As shown in FIG. 3, by bringing cube prism 11 closer to the optical waveguide portion 3, the light can be transmitted through the cube prism 11 by utilizing evanescent wave occurring in total reflection on the surface A opposed to cube prism 11 of the optical waveguide portion 3. The transmission efficiency $\eta$ is determined by the gap size $Z_G$ and is also influenced by the refractive index $n_2$ of the medium, which fills the gap.

Figure 4:
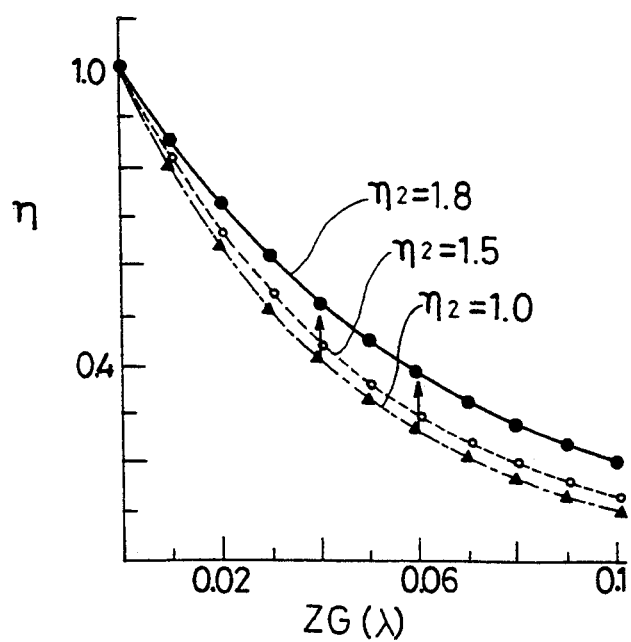
FIG. 4 is a diagram showing the relationship between the gap and the refractive index of the medium filled into the gap or transmission efficiency.

The relationship between the transmission efficiency $\eta$ and the gap $Z_G$ or refractive index $n_2$ of the medium is shown in FIG. 4. As it is evident from FIG. 4, the smaller said gap $Z_G$ becomes, or the higher the refractive index $n_2$ of the medium is, the more the evanescent area is extended outwardly from said opposed surface A. Thus, the transmission efficiency to the prism can be increased.

Further, as it is evident from FIG. 4, the leaking light enough for the measurement can be obtained even when the gap $Z_G$ is not 0. This reveals that measurements can be made with mechanical contact where smaller gaps may partially be present when judged in micro order.

By mechanically attaching the cube prism 11 to the optical waveguide portion 3 in close contact, the leaking light 4 can be obtained, and the refractive index of the optical waveguide portion 3 can be measured.

As described above, there is no need to provide the shielding plate 6 as described in the conventional example because the portion of the detector closer to the center is notched in semi-circular form and the notched edge has an exit angle $\beta_{min}$ of the leaking light. When the indicate point of the laser beam is scanned in the direction of the thickness of the optical waveguide portion 3, or the direction of crossing at right angles with the above direction by proper means, a computing element (not shown) calculates the distribution of refractive index according to the equations (5) and (6) based on signals from the detector 5. Various shapes of the detector can be conceived. It may be in rectangular form, and the edge closer to the center can be separated from the optical waveguide portion 3.

Figure 5:
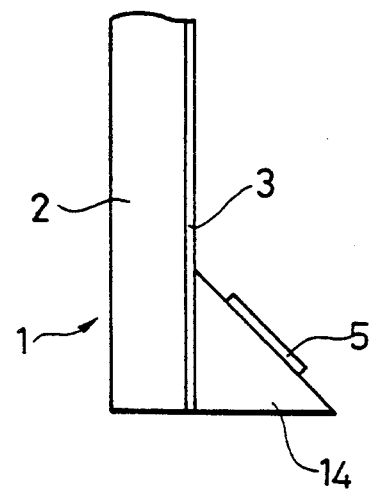
FIG. 5 is a drawing for explaining another embodiment of the invention.

Description is now given on another embodiment in connection with FIG. 5.

In this embodiment, a triangular prism 14 is provided in close contact with the optical waveguide portion 3, and said detector 5 is attached on the inclined surface 15 of the triangular prism 14.

By changing the prism to a triangular prism 14, even under the condition where the incident angle of the leaking light entering the detector is closer to or higher than the critical angle, the incident angle of the leaking light is lower than the critical angle. This makes it possible to receive effectively the leaking light and to make measurement.

Figure 6:
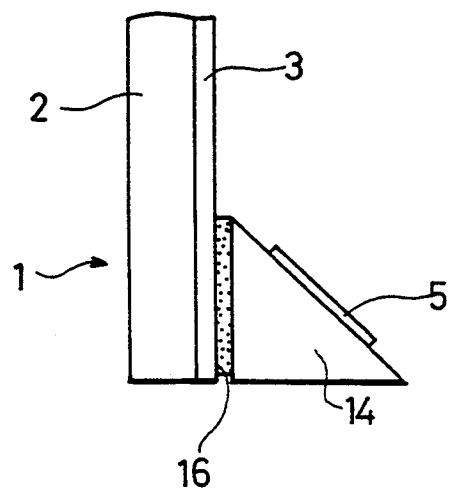
FIG. 6 is a drawing for explaining still another embodiment of the invention.

As described above, the transmission efficiency $\eta$ can be increased by filling the medium with higher refractive index into the gap between the prism and the optical waveguide portion. In the embodiment of FIG. 6, liquid film 16 is placed between the prism 14 and the optical waveguide portion 3. The presence of this liquid film 16 makes it possible to increase the transmission efficiency and to measure even when the roughness of the contact surface of optical waveguide is inaccurate.

Figure 7:
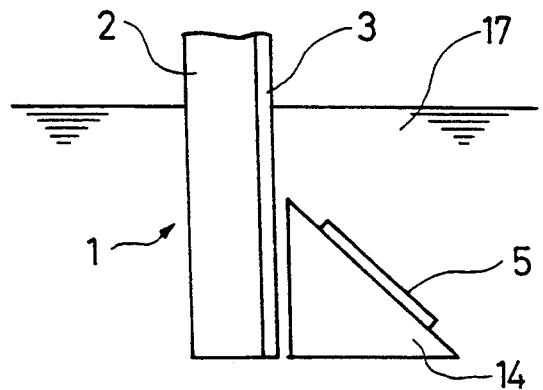
FIG. 7 shows another embodiment of the invention.

From the same reason, the prism 14 may be immersed in the medium liquid 17 as shown in FIG. 7.

Needless to say, the loss of light quantity due to Fresnel reflection on the boundary surface can be decreased by replacing the medium liquid 17 with the air even when the refractive index of said liquid film 16 and the medium liquid 17 is somewhat lower than the refractive index of said optical waveguide unit 3 and the prism 14 or even when the contact is not close enough and gap is present. Particularly, effective results can be obtained in case optical waveguide portion 3 and prism 14 are made of the materials having the refractive index of 2.0 or more.

Figure 8:
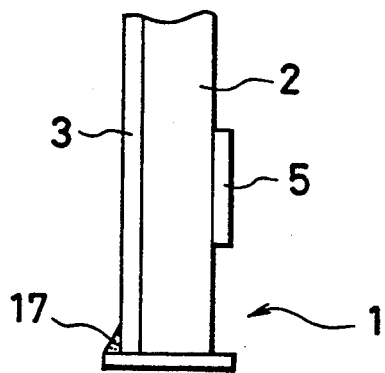
FIG. 8 shows still another embodiment of the invention.

In the above embodiment, solid prisms 11 and 12 are used as having the refractive index of $n_L$ in the equation (1), whereas the substrate portion 2 can be used as having this refractive index of $n_L$. Namely the detector 5 is attached on the surface opposite to the side where optical waveguide portion 3 of the substrate portion 2 is formed as shown in FIG. 8.

In this case, the refractive index $n_L$ of the equation (1) is to be the refractive index $n_S$ of the substrate portion 2. If $n_L = n_S$, the proportional constant a of the equation (6) cannot be obtained. Thus, the reference liquid 17 having the refractive index $n_r$ closer to the refractive index $n_S$ of the substrate is used in slight quantity.

The closer $n_r$ is to $n_S$, the higher the accuracy for determining said proportional constant is, and the more the reliability of the absolute value of the refractive index distribution n(r) of the optical waveguide is increased.

There is no need to use this reference liquid always for the measurement of refractive index distribution of optical waveguide. It can be used only for the calibration of the constant.

Figure 9:
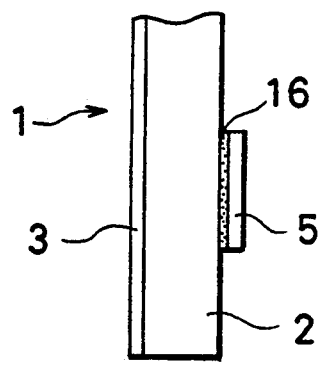
FIG. 9 shows another embodiment of this invention.
Figure 10:
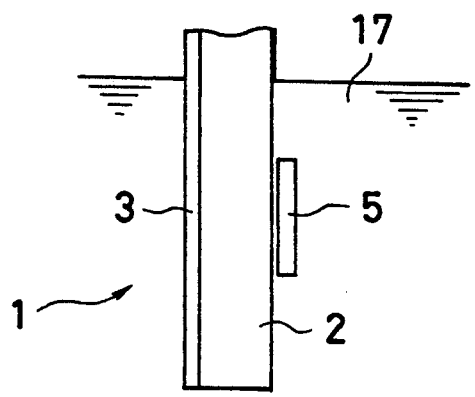
FIG. 10 shows another embodiment of this invention.

FIG. 9 shows an embodiment, in which liquid film 16 is placed between the substrate portion 2 and the detector 5 in order to decrease the loss of light quantity due to Fresnel reflection, and FIG. 10 shows an embodiment with the detector 5 immersed in the medium liquid 17.

Figure 11:
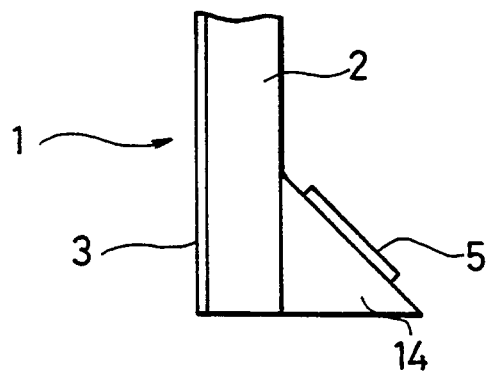
FIG. 11 shows another embodiment of the invention.

FIG. 11 represents an embodiment having the substrate with higher refractive index.

In this embodiment, the measurement light is leaked through a triangular prism 14 by utilizing evanescent wave, using a triangular prism having refractive power closer to the refractive index of the substrate portion 2. A triangular prism 14 is used in this embodiment in order to have the incident angle of the leaking light to the detector 5 to lower than the critical angle.

It is needless to say that the transmission efficiency can be increased by placing the liquid film 16 between the substrate 2 and the triangular prism 14 or by immersing into the medium liquid.

Figure 12:
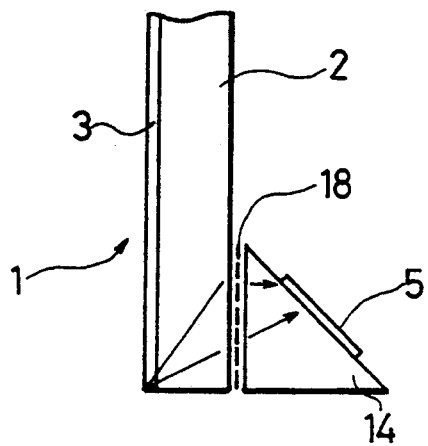
FIG. 12 shows still another embodiment of this invention.

In the embodiment of FIG. 12, transmission efficiency of luminous flux is further increased.

Figure 13:
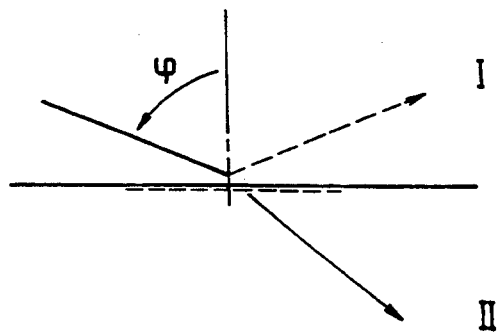
FIG. 13 shows the relationship between the light and the diffraction grating on boundary surface.

As shown in FIG. 13, even in case the light at the medium I enters the medium II at an angle $\phi$ exceeding the critical angle causing total reflection, the light can be obtained towards the medium II at the diffraction angle matching the pitch of the diffraction grating, if diffraction grating is provided on the boundary surface. This is the so-called grating coupler.

Figure 14:
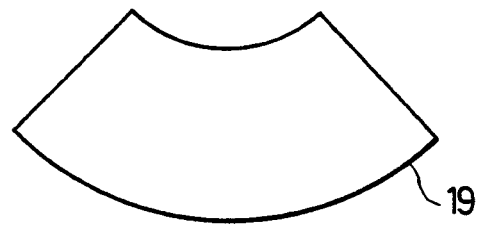
FIG. 14 shows an example of the shape of a holographic lens to be used in the invention.

The embodiment based on this principle is given in FIG. 12. In this embodiment, white and black grating pattern is printed on thin film 18 to form a hologram of amplitude-transmitting type or a hologram of phase type, and this film 18 is brought into close contact between the substrate 2 and the prism 14. Or, a hologram film is also comprised by forming a hologram directly on the surface of triangular prism 14. Further, by forming this grating pattern into curve, a so-called holographic lens is obtained. This makes it possible to converge the measuring luminous fluxes and to obtain high efficiency even when the detector 5 is small. In this case, the role of spatial filter can be given to the diffraction grating by forming the holographic lens 19 in theform as shown in FIG. 14 instead of forming a notched portion on the detector. It is needless to say that the transmission efficiency can be increased by immersing into the medium liquid 17 in this embodiment.

As described above, it is possible according to the present invention to measure the distribution of refractive index of optical waveguide portion even when there is no immersion liquid having the refractive index approximately equal to that of the optical waveguide portion when the distribution of refractive index of optical waveguide portion is measured. This makes the measuring operation much easier and provides high safety because there is no need to use the immersion liquid with high possibility of danger.

What is claimed is:

1. An apparatus for measuring cross-sectional distribution of refractive index of an optical waveguide by RNF method, comprising a projection system for scanning luminous flux for measurement across one end surface of the optical waveguide portion arranged on one side of a substrate portion, a prism member having refractive index close to that of the substrate portion and placed in close contact with the surface of the optical waveguide portion, and a light receiving unit arranged to receive the light leaking from the optical waveguide portion and passing through the prism member, whereby cross-sectional distribution of refractive index of the optical waveguide is measured by change of light quantity entering the light receiving unit as the incident point of the luminous flux for measurement is moved during scanning.

2. An apparatus for measuring cross-sectional distribution of refractive index of an optical waveguide by RNF method according to claim 1, wherein a liquid film is placed between the optical waveguide unit and the prism member.

3. An apparatus for measuring cross-sectional distribution of refractive index of an optical waveguide by RNF method according to claim 1, wherein prism member is immersed in medium liquid.

4. An apparatus for measuring cross-sectional distribution of refractive index of an optical waveguide by RNF method, comprising a projection system for scanning luminous flux for measurement across one end surface of the optical waveguide portion arranged on one side of a substrate portion, and a light receiving unit placed close to the surface of the substrate portion on the side opposite to the optical waveguide portion and receiving the light leaking from the waveguide among luminous fluxes for measurement, whereby cross-sectional distribution of refractive index of the optical waveguide is measured by change of light quantity entering the light receiving unit as the incident point of the luminous flux for measurement is moved during scanning.

5. An apparatus for measuring cross-sectional distribution of refractive index of an optical waveguide by RNF method according to claim 4, wherein liquid film is placed between the light receiving unit and the substrate.

6. An apparatus for measuring cross-sectional distribution of refractive index of an optical waveguide by RNF method according to claim 4, wherein the light receiving unit is immersed in the medium liquid.

7. An apparatus for measuring cross-sectional distribution of refractive index of an optical waveguide by RNF method, comprising a projection system for scanning luminous flux for measurement across one end surface of the optical waveguide portion arranged on one side of a substrate portion, a prism member having refractive index close to that of the substrate portion and placed in close contact with the surface of the substrate portion opposite to the optical waveguide portion, and a light receiving unit arranged to receive the light leaking from the optical waveguide portion and passing through the prism member, whereby cross-sectional distribution of refractive index of the optical waveguide is measured by change of light quantity entering the light receiving unit as the incident point of the luminous flux for measurement is moved during scanning.

8. An apparatus for measuring cross-sectional distribution of refractive index of an optical waveguide by RNF method according to claim 7, wherein liquid film is placed between the substrate portion and the prism member.

9. An apparatus for measuring cross-sectional distribution of refractive index of an optical waveguide by RNF method according to claim 8, wherein prism member is immersed in medium liquid.

10. An apparatus for measuring cross-sectional distribution of refractive index of an optical waveguide by RNF method according to any one of claims 1, 2, 3, 7, 8 and 9, wherein hologram film is placed on the surface of the prism which is placed in close contact with the surface of the optical waveguide portion.

11. An apparatus for measuring cross-sectional distribution of refractive index of an optical waveguide by RNF method according to any one of claims 1, 2, 3, 7, 8 and 9, wherein prism member is a triangular prism.

* * * * *